US011604098B2

(12) United States Patent
Price et al.

(10) Patent No.: US 11,604,098 B2
(45) Date of Patent: Mar. 14, 2023

(54) DISTANCE CORRECTION FOR BODY TEMPERATURE ESTIMATION

(71) Applicant: Microsoft Technology Licensing, LLC, Redmond, WA (US)

(72) Inventors: Raymond Kirk Price, Redmond, WA (US); Christopher Douglas Edmonds, Carnation, WA (US); Michael Bleyer, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 178 days.

(21) Appl. No.: 16/909,657

(22) Filed: Jun. 23, 2020

(65) Prior Publication Data

US 2021/0396586 A1 Dec. 23, 2021

(51) Int. Cl.
*G09G 5/00* (2006.01)
*G01J 5/02* (2022.01)
(Continued)

(52) U.S. Cl.
CPC ............ *G01J 5/027* (2013.01); *G01J 5/0025* (2013.01); *G06T 11/60* (2013.01); *G06V 10/143* (2022.01);
(Continued)

(58) Field of Classification Search
CPC ..... B65B 3/025; B29C 65/08; B29C 55/1122; B29C 66/43122; B29C 66/80
(Continued)

(56) References Cited

U.S. PATENT DOCUMENTS 5,555,512 A * 9/1996 Imai ..................... G08B 13/194
250/342
2010/0172567 A1* 7/2010 Prokoski ................. G06K 9/00
348/47
(Continued)

FOREIGN PATENT DOCUMENTS

WO 2019209887 A1 10/2019

OTHER PUBLICATIONS

Aryal, et al., "Skin Temperature Extraction Using Facial Landmark Detection and Thermal Imaging for Comfort Assessment", In Proceedings of the 6th ACM International Conference on Systems for Energy-Efficient Buildings, Cities, and Transportation, Nov. 13, 2019, pp. 71-80.
(Continued)

*Primary Examiner* — Gordon G Liu
(74) *Attorney, Agent, or Firm* — Alleman Hall Creasman & Tuttle LLP

(57) ABSTRACT

A method for estimating human body temperature includes receiving, via a thermal camera, a thermal image captured of a real-world environment, the thermal image including thermal intensity values for each of a plurality of pixels of the thermal image. A position of a human face is identified within the thermal image, the human face corresponding to a human subject. An indication of a distance between the human subject and the thermal camera is received. Based on the distance, a distance correction factor is applied to one or more thermal intensity values of one or more pixels corresponding to the human face to give one or more distance-corrected thermal intensity values. Based on the one or more distance-corrected thermal intensity values an indication of a body temperature of the human subject is reported.

20 Claims, 10 Drawing Sheets

(51) Int. Cl.
  *G06V 10/56*   (2022.01)
  *G06V 10/143*  (2022.01)
  *G06V 40/16*   (2022.01)
  *G06V 20/64*   (2022.01)
  *G01J 5/00*    (2022.01)
  *G06T 11/60*   (2006.01)

(52) U.S. Cl.
  CPC ............ *G06V 10/56* (2022.01); *G06V 20/647* (2022.01); *G06V 40/166* (2022.01); *G01J 2005/0077* (2013.01); *G06T 2210/41* (2013.01)

(58) Field of Classification Search
  USPC .......................................... 53/266.1; 345/633
  See application file for complete search history.

(56) References Cited

U.S. PATENT DOCUMENTS

| | | |
|---|---|---|
| 2013/0124039 A1 | 5/2013 | Abreu |
| 2015/0204556 A1* | 7/2015 | Kusukame ............ G01J 5/0025 250/338.3 |
| 2015/0379851 A1 | 12/2015 | Diels |
| 2018/0094982 A1* | 4/2018 | Tzvieli ................. G01J 5/0265 |
| 2019/0080431 A1 | 3/2019 | Choi et al. |
| 2020/0121245 A1* | 4/2020 | Barclay ............... A61B 5/1072 |

OTHER PUBLICATIONS

"International Search Report and Written Opinion issued in PCT Application No. PCT/US21/026497", dated Jul. 29, 2021, 14 Pages.

\* cited by examiner

200

```
┌─────────────────────────────────────────────┐
│ RECEIVE A THERMAL IMAGE CAPTURED OF A REAL- │
│ WORLD ENVIRONMENT, THE THERMAL IMAGE         │
│ INCLUDING THERMAL INTENSITY VALUES FOR EACH │
│ OF A PLURALITY OF PIXELS                     │
│                                         202  │
└─────────────────────────────────────────────┘
                      │
                      ▼
┌─────────────────────────────────────────────┐
│ IDENTIFY A POSITION OF A HUMAN FACE WITHIN  │
│ THE THERMAL IMAGE, THE HUMAN FACE            │
│ CORRESPONDING TO A HUMAN SUBJECT             │
│                                         204  │
└─────────────────────────────────────────────┘
                      │
                      ▼
┌─────────────────────────────────────────────┐
│ RECEIVE AN INDICATION OF A DISTANCE BETWEEN │
│ THE HUMAN SUBJECT AND THE THERMAL CAMERA    │
│                                         206  │
└─────────────────────────────────────────────┘
                      │
                      ▼
┌─────────────────────────────────────────────┐
│ APPLY A DISTANCE CORRECTION FACTOR TO ONE OR│
│ MORE THERMAL INTENSITY VALUES CORRESPONDING │
│ TO THE HUMAN FACE TO GIVE DISTANCE-CORRECTED│
│ THERMAL INTENSITY VALUES                     │
│                                         208  │
└─────────────────────────────────────────────┘
                      │
                      ▼
┌─────────────────────────────────────────────┐
│ REPORT AN INDICATION OF A BODY TEMPERATURE  │
│ OF THE HUMAN SUBJECT BASED ON THE DISTANCE- │
│ CORRECTED THERMAL INTENSITY VALUES           │
│                                         210  │
└─────────────────────────────────────────────┘
```

FIG. 2

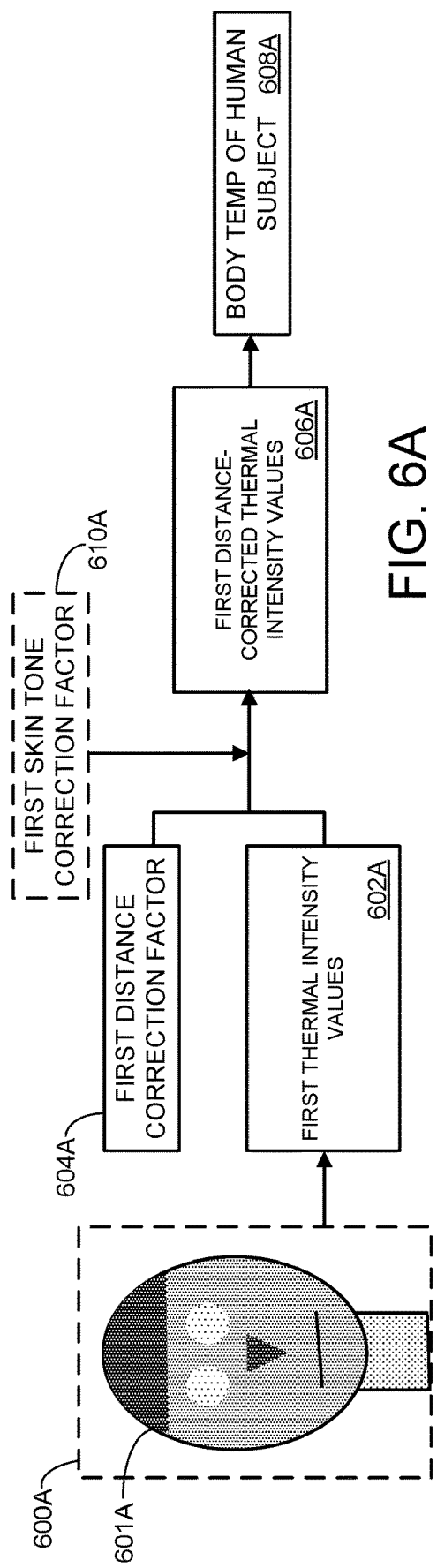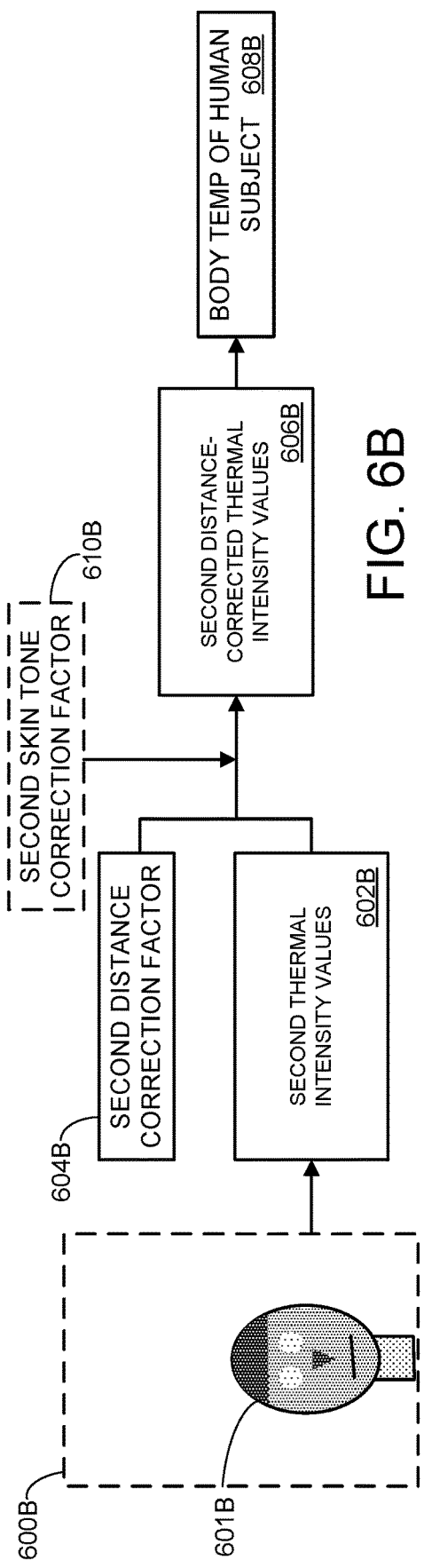

DISTANCE CORRECTION FOR BODY TEMPERATURE ESTIMATION

BACKGROUND

Relative temperatures of objects in an environment may be estimated from thermal images. Pixels of a thermal image may encode thermal intensity values that express relative amounts of thermal energy received by the thermal camera from objects in the environment. The amount of thermal energy received by a thermal camera from an object may vary depending on the distance between the camera and the object.

BRIEF DESCRIPTION OF THE DRAWINGS

FIG. 2 illustrates an example method for estimating human body temperature.

FIGS. 6A and 6B schematically illustrate distance correction of thermal intensity values of two human subjects.

DETAILED DESCRIPTION

Figure 1:
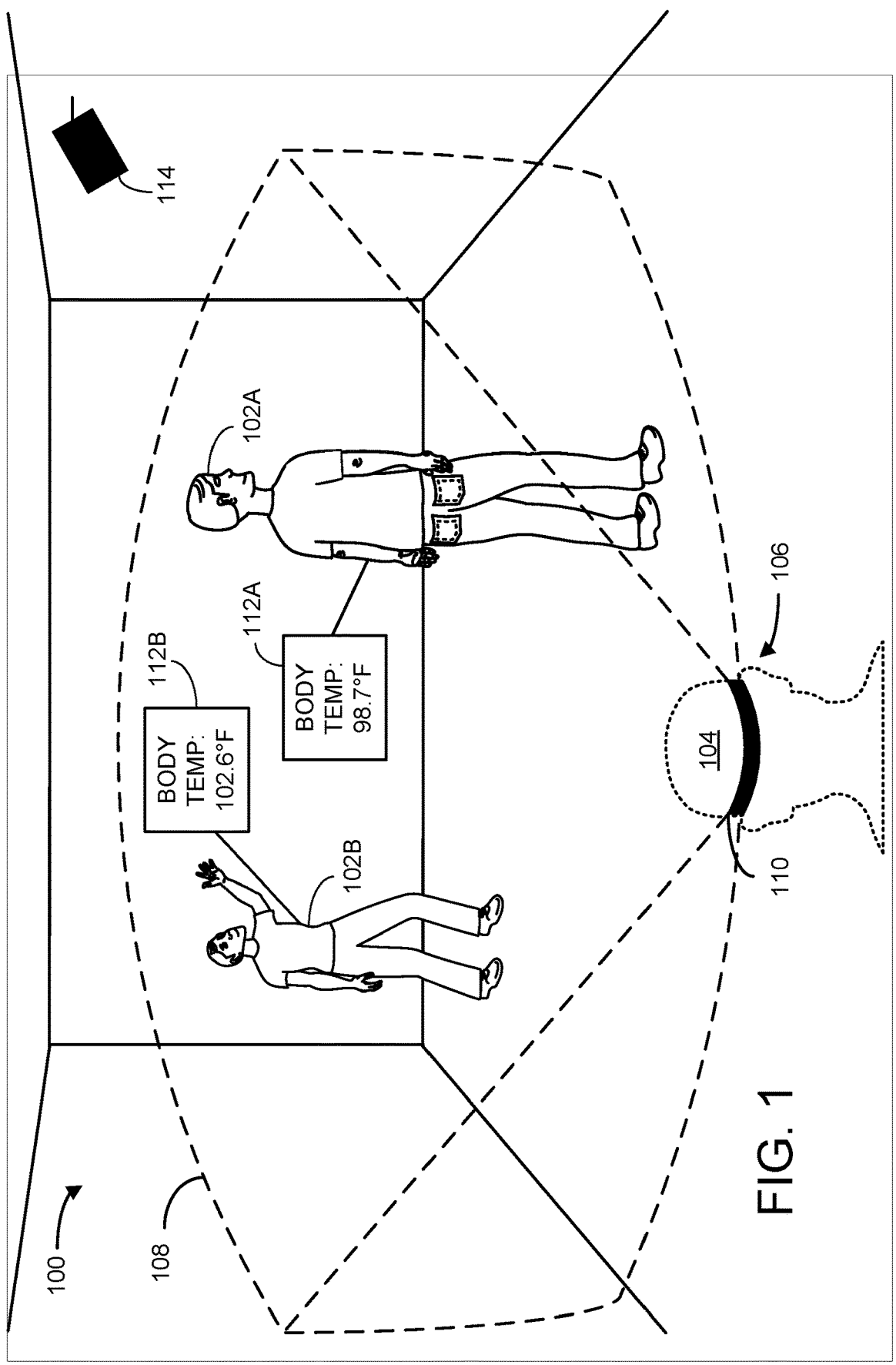
FIG. 1 schematically depicts reporting of indications of body temperatures of human subjects.

In some cases, a computing device may be used to estimate and report an indication of a body temperature of a human subject. This is schematically illustrated in FIG. 1, which shows a real-world environment 100 including two example human subjects 102A and 102B. In environment 100, a user 104 equipped with a head-mounted display device 106 has a field-of-view 108, indicating an area in which virtual content presented by a near-eye display 110 of the head-mounted display device may be visible to the user. Via the near-eye display, the head-mounted display device is displaying indications 112A and 112B of estimated body temperatures of the human subjects.

An indication of a body temperature of a human subject may take any suitable form. In the example of FIG. 1, the estimated body temperatures of the human subjects are numerically represented on the near-eye display of the head-mounted display device, such that the body temperatures are displayed at screen-space positions on the near-eye display at or near positions corresponding to the human subjects. In other examples, as will be described in more detail below, the indications of the body temperatures of the human subjects may be reported in other suitable ways (e.g., non-numerically). Furthermore, indications of human body temperatures need not be presented on near-eye displays, but rather may be presented on any suitable electronic display in any suitable manner.

The body temperatures of human subjects may be estimated in any suitable way. It will be understood that a human's internal body temperature varies across different parts of the body. Thus, for the purposes of this disclosure, the "body temperature" of a human subject will refer to the subject's core body temperature, which is often used for the purposes of medical diagnosis. This may differ from the body temperature estimated based on thermal intensity values corresponding to a subject's skin. Thus, for the purposes of this disclosure, outputting an estimated body temperature may in some cases include correcting a skin-based body temperature estimate to give a core body temperature—e.g., by adding 0.5-1.0° F. to the skin-based temperature.

In some examples, a thermal image of the real-world environment may be captured by a thermal camera, the thermal image having thermal intensity values for each of a plurality of pixels of the thermal image, including pixels corresponding to human subjects that may be in the environment. The thermal camera may in some cases be integrated into a head-mounted display device (or other computing device configured to perform functions described herein), or may alternatively be a standalone camera or a component of a separate camera system, such as camera system 114. The thermal intensity values of the thermal image encode the amount of thermal energy emitted by the objects in the real-world environment and received by the thermal camera. In this manner, the relative temperatures of the objects in the real-world environment may be estimated based on their corresponding thermal intensity values in the thermal image.

However, the amount of thermal energy received by a thermal camera from a human subject at a particular temperature may depend on the distance between the subject and the thermal camera. This may be particularly true when the thermal camera lacks a radiometric lens disposed before other optical elements of the thermal camera. Even in the case where a radiometric lens is used, the distance between a human subject and a thermal camera may still affect how the subject is represented in the thermal image. For instance, as the distance between the thermal camera and human subject increases, relatively fewer pixels of the thermal image will be used to represent relatively larger portions of the human subject. Thus, high-intensity regions of the human subject may be averaged or subsampled with relatively lower-intensity portions of the human subject, creating the illusion that the human has an overall lower thermal intensity.

For example, in FIG. 1, subjects 102A and 102B are at different distances away from the camera, and thus will exhibit this distance-dependent intensity attenuation. This can make it difficult, for example, to identify human subjects in a thermal image having elevated body temperatures (e.g., consistent with a fever), as two different human subjects having different distances away from a thermal camera will register differently within a thermal image, even when the two users have the same core body temperature. Similarly, it may be difficult to discern when two human subjects having different distances away from the thermal camera have significantly different body temperatures (e.g., one feverish and one normal).

Accordingly, the present disclosure is directed to techniques for estimating human body temperature based on an identified distance of a human subject away from a thermal camera. Specifically, after identifying the position of the face of a human subject within a thermal image, an indication of a distance of the human subject away from the camera is received. Then, based on the distance, a distance correction factor is applied to one or more thermal intensity values corresponding to the human face. Based on these distance-corrected thermal intensity values, an indication of a body temperature of the human subject is reported. In this manner, the body temperatures of human subjects may be more accurately estimated, even in cases where the human subjects are disposed at variable distances away from the thermal camera.

FIG. 2 illustrates an example method 200 for estimating body temperature. Method 200 may be implemented on any suitable computing system, having any suitable form factor and hardware configuration. Steps of method 200 may be distributed between any number of different computing devices. As examples, computing devices used to implement method 200 may include desktop computers, laptop computers, servers, smartphones, tablets, augmented/virtual/mixed reality devices, wearable devices (e.g., fitness watches), media centers, vehicle computer systems, dedicated camera/monitoring systems, etc. In some examples, method 200 may be implemented via computing system 1000 described below with respect to FIG. 10.

Furthermore, method 200 is primarily described with respect to a single human subject, and results in reporting an indication of the body temperature of the human subject. However, it will be understood that steps of method 200 may be performed for any number of human subjects, who may be distributed between any number of different thermal images. In other words, each of the steps of method 200 may be performed for two or more human subjects, either simultaneously (e.g., two or more human subjects are visible in a same thermal image) or sequentially (e.g., two different human subjects are identified in two different thermal images). In cases where method 200 is applied to two or more human subjects, each human subject may have a different distance away from the thermal camera.

At 202, method 200 includes receiving, via a thermal camera, a thermal image captured of a real-world environment, the thermal image including thermal intensity values for each of a plurality of pixels of the thermal image. As discussed above, a thermal camera may be integrated into a computing device that performs one or more steps of method 200 beyond image capture. Alternatively, the thermal camera may be a standalone camera, or a component of a separate camera system. For example, FIG. 1 schematically depicts an example camera system 114, which may include at least a thermal camera. Thus, the one or more computing devices configured to implement steps of method 200 may in some case receive thermal images (and/or other images) from remote cameras. Camera system 114 may additionally include other types of cameras utilizing any camera technology. As examples, camera system 114 may include a thermal camera, visual light camera, and/or depth camera. In some cases, camera system 114 may include processing componentry usable to implement steps of method 200.

Figure 3:
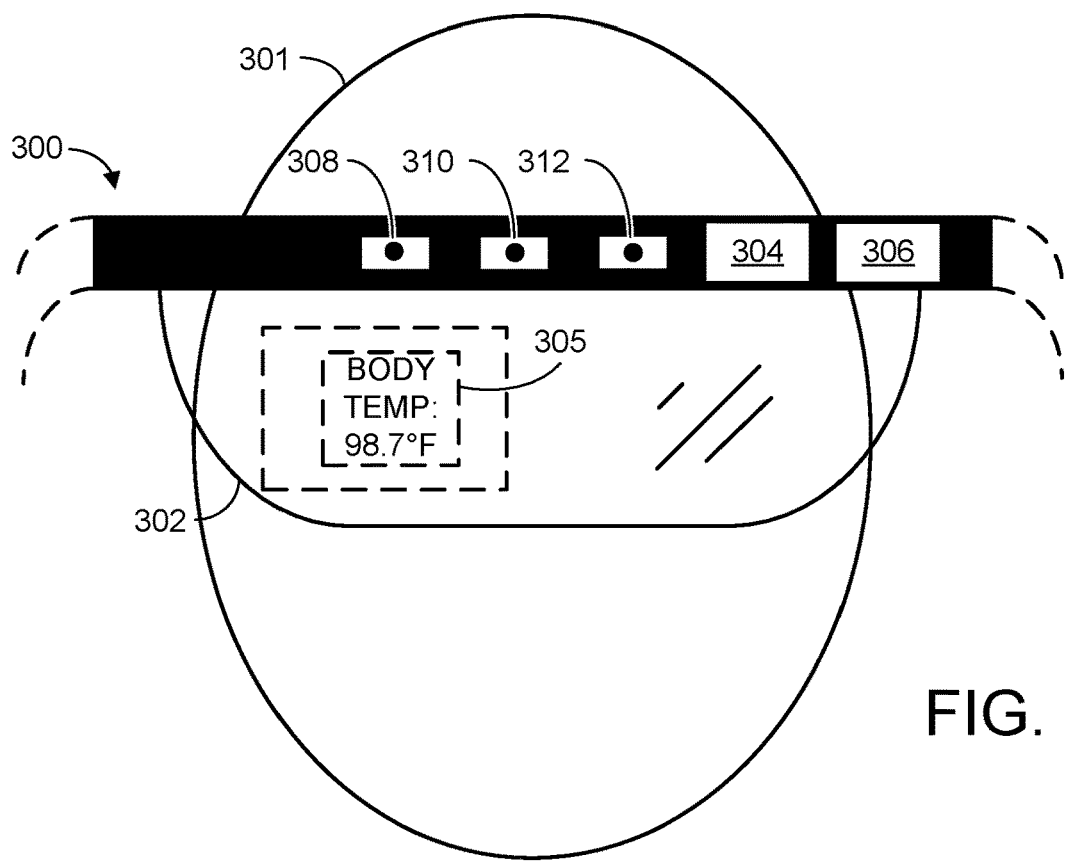
FIG. 3 schematically depicts an example head-mounted display device.

As another example, FIG. 3 schematically depicts a head-mounted display device 300 being worn on a user head 301. Head-mounted display device 300 includes a near-eye display configured to display virtual images to the user's eyes. Virtual images displayed on a near-eye display may take any suitable form, and may be provided as part of virtual and/or augmented reality experiences. In the example of FIG. 3, head-mounted display device 300 is displaying an indication 305 of an estimated body temperature of a human subject. However, as will be discussed in more detail below, indications of body temperature may take any suitable form and may be displayed via any suitable electronic display.

Head-mounted display device 300 includes a storage machine 304 that may hold instructions executable by a logic machine 306 to perform one or more steps of method 200, and/or any other suitable computer functions. Additional details with respect to the storage machine and logic machine are described below with respect to FIG. 10.

Head-mounted display device 300 also includes several cameras 308, 310, and 312. In one example, camera 308 may be a thermal camera, while camera 310 is a visible light camera and camera 312 is a depth camera. However, computing devices described herein may include any suitable collection of cameras useable to image environments and estimate body temperatures of human subjects. Each of these cameras may use any suitable technology.

In general, a "thermal camera" may include any imaging system configured to receive and encode thermal energy (e.g., infrared light) from objects in an environment. A thermal camera may typically be sensitive to light in the 8-14 μm range that detects blackbody radiation emitted by objects in an environment. The amount of radiation emitted by any particular object may be dependent on the object's emissivity (or the relative power of a surface to radiate heat). In some examples, a thermal camera may include a radiometric lens disposed before other optical elements of the thermal camera. Similarly, when included, visible light and depth cameras may take any suitable form. For instance, a depth camera may be a structured light depth camera or a time-of-flight depth camera. Any or all of the cameras of computing devices described herein may capture images having any suitable resolution, and the images may be captured with any suitable frame rate.

Figure 4:
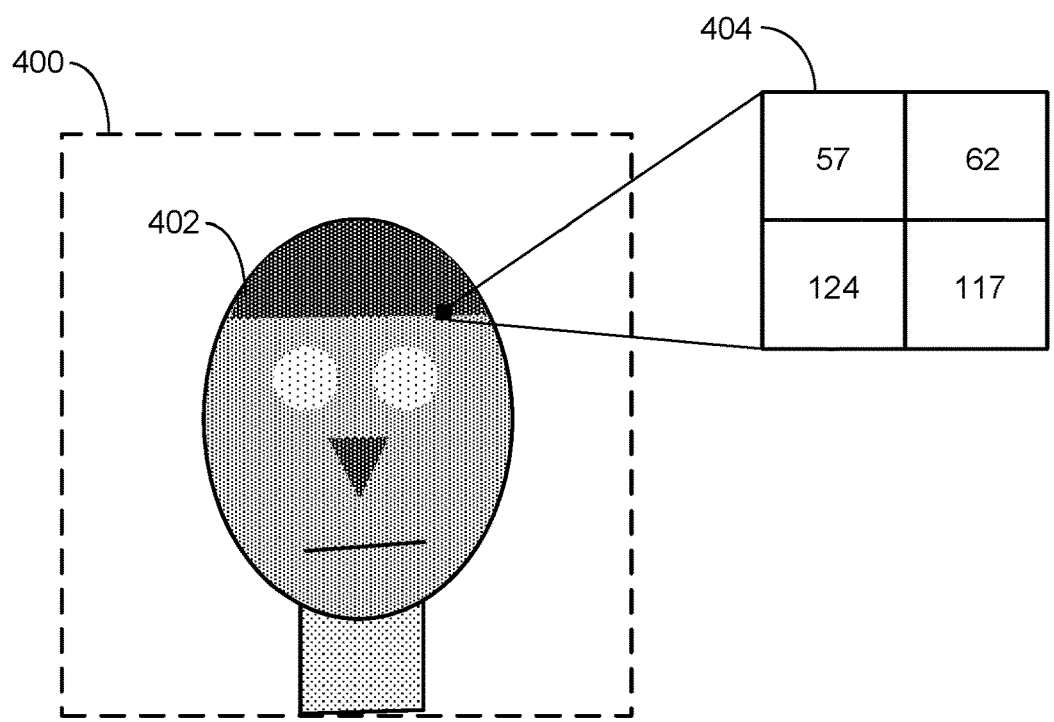
FIG. 4 schematically depicts example thermal-intensity values of a thermal image depicting a human subject.

As described herein, thermal cameras capture "thermal images" of real-world environments. One example thermal image 400 is schematically shown in FIG. 4. Thermal image 400 depicts an example human subject 402. Specifically, thermal image 400 includes a plurality of thermal intensity values 404, which correspond to four individual pixels of the thermal image. It will be understood that the thermal image may include any suitable number of pixels, and each pixel may have a corresponding thermal-intensity value.

In some cases, relatively higher thermal intensity values may correspond to regions in the imaged scene that are emitting relatively more thermal energy. In FIG. 4, pixels of thermal image 400 having relatively higher thermal intensity values are represented with relatively lighter shading. Thus, as can be seen, the face of human subject 402 is not emitting thermal energy uniformly. Rather, human faces typically exhibit some degree of temperature variation—e.g., the regions around a human's eyes are often higher temperature than regions corresponding to the human's nose, hair, ears, etc. This is reflected in FIG. 4, as relatively higher-temperature portions of the human's face have relatively higher thermal-intensity values in the thermal image.

A thermal image may take the form of any suitable data structure that includes a plurality of thermal intensity values, which in turn encode thermal energy received by the thermal camera from objects in an environment. In some cases, thermal intensity values may take the form of grey-level counts, which may have any suitable value. For example, grey-level counts may be expressed as a range between 0 and 255, or a different suitable quantization may be used. The present disclosure primarily describes thermal images as having a plurality of pixels. However, it will be understood that a "thermal image" need not be displayed on an electronic display, or otherwise visually represented in any manner. Rather, a thermal image including a plurality of pixels may in some cases be a purely non-visual data structure. Alternatively, and as will be described in more detail below, some representation of a thermal image may in some cases be visually displayed for review by a human user.

Returning to FIG. 2, at 204, method 200 includes identifying a position of a human face within the thermal image, the human face corresponding to a human subject. In some cases, the position of the human face may be identified after receiving, via a second camera sensitive to a different spectrum of light from the thermal camera (e.g., camera 310 of head-mounted display device 300), a second image captured of the real-world environment. The second camera may, for example, be a visible light camera, while the second image may be a visible light image. The device may then determine correspondences between pixels of the second image and pixels of the thermal image. For example, after identifying the position of the human face within the second image, the position of the human face within the thermal image may be identified based on the pixel-to-pixel correspondences between the two images.

Figure 5:
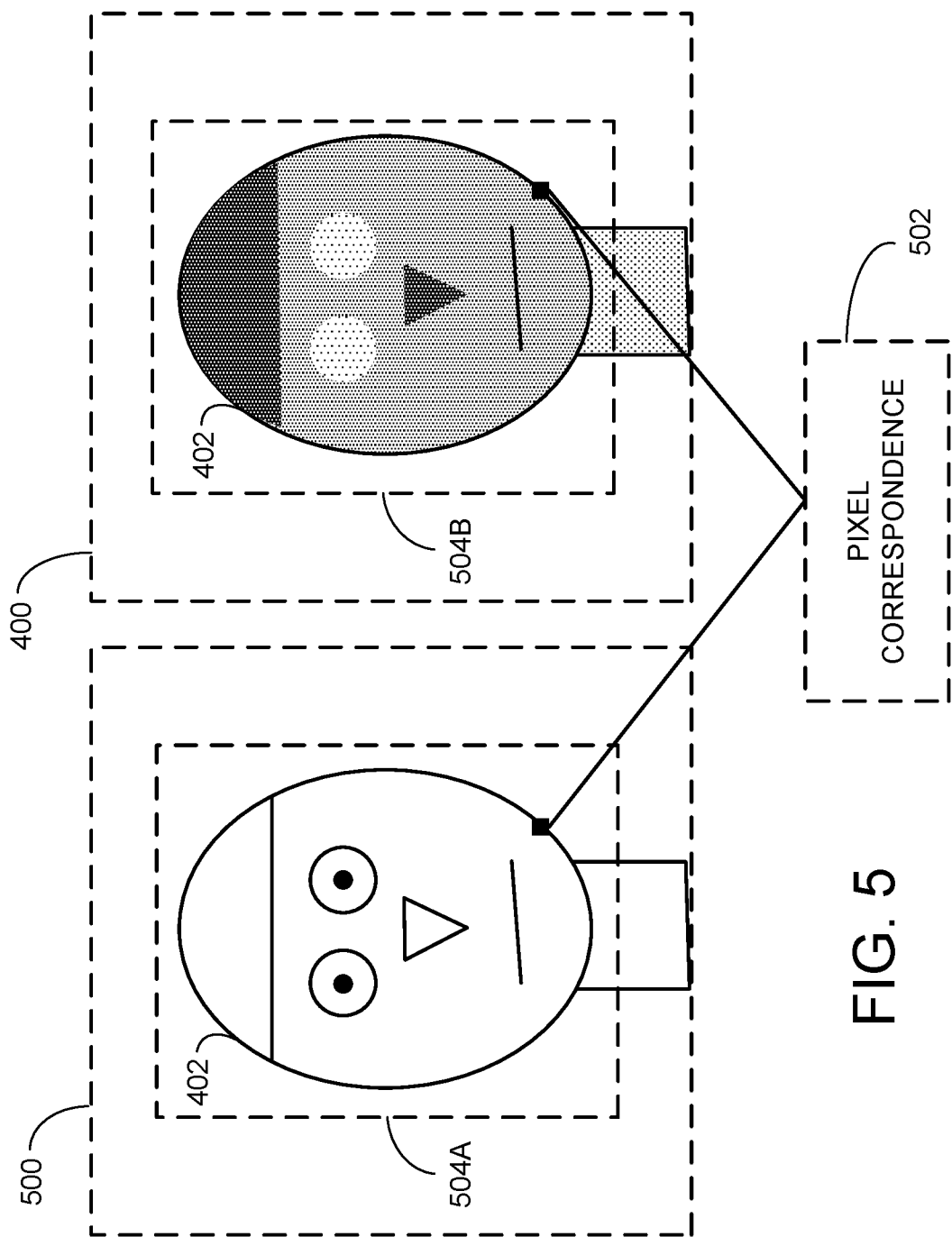
FIG. 5 schematically depicts pixel correspondences between a thermal image and a second image.

This is schematically illustrated in FIG. 5. Specifically, FIG. 5 again includes thermal image 400 depicting human subject 402. FIG. 5 also includes a second image 500, also depicting human subject 402. The computing device identifies a plurality of pixel-to-pixel correspondences 502 between image 500 and image 400. Such correspondences may be identified in any suitable way. The thermal image and second image may be captured by different cameras (e.g., cameras 308 and 310) having different positions and perspectives. When the relative positions and perspectives of the two cameras are known, pixels of images captured by each camera may be projected into a common frame of reference—e.g., relative to a virtual camera. In this manner, it may be determined which pixels of one image (e.g., image 500) correspond to the same real-world features as the other image (e.g., image 400). Thus, when a position 504A of a face of human subject 402 in image 500 is identified, the computing device may determine which pixels of image 400 correspond to the same position 504B of the face within the thermal image. In other examples, however, the position of one or more human faces within a thermal image may be identified in other suitable ways.

The face of a human subject may be identified in any suitable way. In some examples, any suitable facial recognition algorithm or technique may be used. For instance, one approach may include using a machine-learning trained classifier to identify pixels in an image (e.g., a visible light or thermal image) predicted to correspond to a human face.

Returning to FIG. 2, at 206, method 200 includes receiving an indication of a distance between the human subject and the thermal camera. As discussed above, when the distance between a human subject and a thermal camera increases, the human subject may appear to have a lower thermal intensity in a thermal image captured by the camera. This may be due to the fact that the thermal camera receives less thermal energy, or because relatively fewer pixels are encoding larger portions of the human, and thus high-intensity regions are averaged with lower intensity regions. For example, human subjects 102A and 102B in FIG. 1 are at different distances away from the camera. Thus, subject 102B may appear to have less thermal intensity in a thermal image than subject 102A, even when both subjects have the same core body temperature. In order to more accurately estimate the body temperature of a human subject, the human subject's distance away from the thermal camera may therefore first be determined.

The distance between a human subject and a thermal camera may be determined in any suitable way. In some examples, this distance may be determined based on depth information collected by a depth camera—e.g., camera 312 of head-mounted display device 300 of FIG. 3. The depth camera may take any suitable form, including a time-of-flight depth camera and a structured light depth camera. In other examples, however, the distance between a thermal camera and a human subject may be determined without the benefit of a depth camera. For instance, a stereoscopic pair of visible light cameras may be used. When two or more subjects are present, the relative distances of each human subject may be estimated by comparing the relative sizes of each subject's head. Alternatively, a single visible light camera may be used, in tandem with a machine-learning trained distance estimation algorithm. As another example, the distance between a thermal camera and a human subject may be manually specified by a human user.

Returning to FIG. 2, at 208, method 200 includes applying, based on the distance, a distance correction factor to one or more thermal intensity values of one or more pixels corresponding to the human face to give one or more distance-corrected thermal intensity values. This is schematically illustrated with respect to FIGS. 6A and 6B. Specifically, FIG. 6A shows an example thermal image 600A of a face of a first human subject 601A.

The computing device identifies one or more thermal intensity values 602A of one or more pixels corresponding to the human face. In some cases, the one or more thermal intensity values to which the distance correction factor is applied may correspond to one or more highest-intensity pixels depicting the human face. In many cases, these pixels may correspond to the skin around the human subject's eyes, and/or the eyes themselves, as is shown in FIG. 6A. In other examples, however, a distance correction factor may be applied to any thermal intensity values identified as corresponding to any part of a human subject.

Continuing with FIG. 6A, a first distance correction factor 604A is applied to the first thermal intensity values 602A to give distance-corrected thermal intensity values 606A. A "distance correction factor" may take any suitable form. Typically, applying a distance correction factor will include scaling thermal intensity values either up or down by some amount that depends on the distance between the human subject and the thermal camera. For example, when human subjects are relatively far from the thermal camera, thermal intensity values corresponding to the face of the human subject may be scaled up, such that they are more consistent with a human subject who is relatively closer to the thermal camera. Alternatively, thermal intensity values corresponding to human subjects that are relatively close to the thermal camera may be scaled down such that they are more consistent with human subjects who are relatively further from the thermal camera.

FIG. 6B schematically shows a different thermal image 600B, corresponding to a face of a second human subject 601B. Notably, second human subject 601B has a greater distance away from the thermal camera than first human subject 601A. Thus, after one or more second thermal intensity values 602B are identified as corresponding to the face of human subject 601B, a second distance correction factor 604B is applied, giving one or more second distance-corrected thermal intensity values 606B. Because the distances of the first and second human subjects are different, the first and distance correction factors are different. Thus, the first and second thermal intensity values, corresponding to the first and second human subjects, may be scaled by different amounts based on the first and second distance correction factors. In some cases, the thermal intensity values of one human subject may be scaled, while the thermal intensity values of the other human subject are not.

The specific distance correction factor applied may be determined in any suitable way. In some cases, the distance correction factor may be determined during factory calibration of a thermal camera. For instance, during calibration, a reference object having a known temperature may be imaged at multiple different distances away from the camera. Because the temperature of the reference object is known, any changes in the thermal intensity values corresponding to the object will likely be due to distance-dependent attenuation. Based on this calibration, the computing device may determine a scaling factor that may be applied to thermal intensity values of an object at any arbitrary distance to give distance-corrected thermal intensity values, which may be equivalent to an object at a predetermined default distance—e.g., 2 meters. The distance correction factor may in some cases be maintained as a lookup table—e.g., the device may store different correction factors for different known distance thresholds. Alternatively, the distance correction factor may be a suitable function that outputs a distance-corrected thermal intensity value, using as inputs the distance between a human subject and a thermal camera, and thermal intensity values corresponding to the human subject.

Additionally, or alternatively, the distance correction factor may be determined via user calibration. In one example, the distance correction factor may be derived by determining a distance-dependent intensity change of thermal intensity values corresponding to a reference human subject, as a distance between the reference human subject and the thermal camera changes over a plurality of thermal images. This is schematically illustrated in FIG. 6C, which shows two more example thermal images 612A and 612B, each depicting the same reference human subject 614.

However, between images 612A and 612B, the distance between the reference human subject and the thermal camera has increased. Thus, by comparing the thermal intensity values 616A corresponding to the reference human subject at the first distance to the thermal intensity values 616B corresponding to the reference human subject at the second distance, the computing device may determine a distance-dependent intensity change 618. Again, because the temperature of the reference human is unlikely to have significantly changed between the two thermal images, any changes in the thermal intensity values corresponding to the reference human will likely be due to distance-dependent attenuation, and the distance correction factor may be derived on this basis.

Figure 6C:
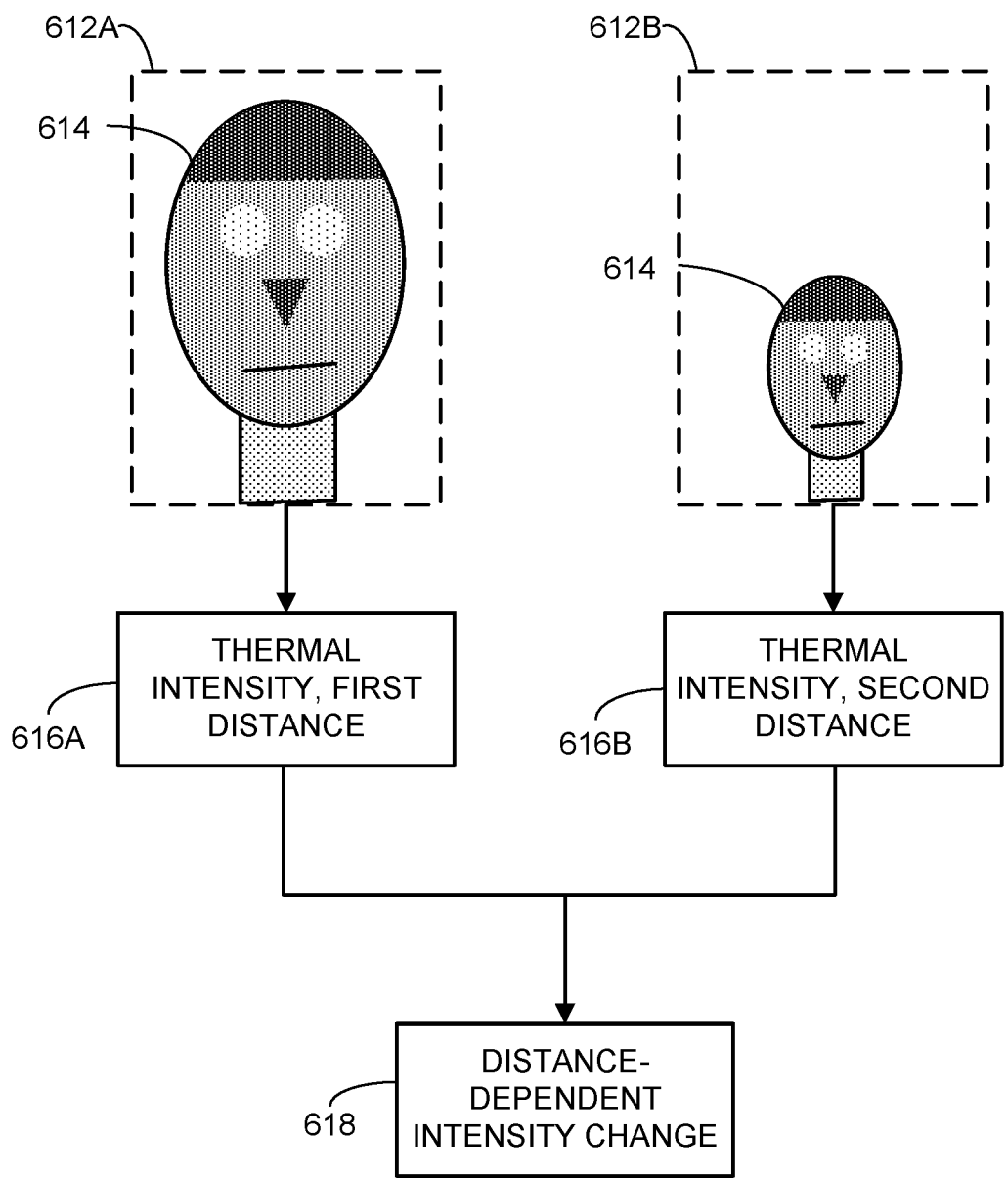
FIG. 6C schematically illustrates deriving a distance-dependent intensity change from thermal images of a reference human subject at different distances.

It will be understood that, while only two images of the reference human subject are used in FIG. 6C, this is not limiting. Rather, in practical scenarios, any number of thermal images may be captured of a reference human subject at any number of different distances away from the thermal camera.

As another example, the distance correction factor may be derived based on identifying a plurality of different human subjects at different distances from the thermal camera in a plurality of different thermal images, and determining a distance-dependent intensity distribution of thermal intensity values corresponding to the plurality of different human subjects. This will be described in more detail below with respect to FIG. 8.

In some examples, the skin tone of a human subject may also be considered when estimating the body temperature of the human subject. For example, the thermal emissivity value of light-colored human skin has been estimated to be approximately 0.95, while the thermal emissivity of dark-colored skin is approximately 0.98. Thus, for a given body temperature, darker-skinned human subjects may have relatively higher thermal intensity values in a thermal image than lighter-skinned human subjects. It may therefore in some cases be beneficial to first identify the skin tone of a human subject, then apply a skin tone correction factor to thermal-intensity values corresponding to the human subject to give tone-corrected thermal intensity values. This may be done in addition to, or as an alternative to, distance correction as described above.

In the examples of FIGS. 6A and 6B, human subjects 601A and 601B may have different skin tones. Thus, a first skin tone correction factor 610A may be applied to the first thermal intensity values 602A corresponding to first human subject 601A. Similarly, a different skin tone correction factor 610B may be applied to the second thermal intensity values 602B corresponding to second human subject 601B. Tone-corrected thermal intensity values may be used to estimate the body temperature of a human subject, in a similar manner to distance-corrected thermal intensity values.

The skin tone of a human subject may be identified in any suitable way. In one example, the skin tone of a human subject may be identified based on the color of a human face in a second image, such as a visible light image. For example, returning briefly to FIG. 5, the color of the face of human subject 402 may be identified based on the colors of pixels identified as corresponding to the position 504A of the human face within image 500. Additionally, or alternatively, the skin tone of a human subject may be identified from images that use non-visible wavelengths, such as images captured by a depth camera. As another example, the skin tone of a human subject may be manually specified by a human user.

Applying a skin tone correction factor may include scaling thermal intensity values for lighter-skinned human subjects up, such that they are more consistent with darker-skinned human subjects. Alternatively, thermal intensity values for darker-skinned human subjects may be scaled down, such that they are more consistent with lighter-skinned human subjects. As another example, thermal intensity values for all human subjects may be scaled up by variable amounts, to give thermal intensity values consistent with a tone-neutral thermal emissivity value—e.g., 1.0.

In some implementations, skin tone correction factors may be predetermined for different specific skin tones. For example, the computing device may maintain a lookup table or similar data structure that defines a plurality of skin tone correction factors for use with a plurality of different skin tones. Alternatively, skin tone correction factors may be dynamically calculated on-the-fly based on a specific identified skin tone of a particular human subject.

Returning to FIG. 2, at 210, method 200 includes reporting an indication of a body temperature of the human subject based on the distance-corrected thermal intensity values. This is schematically illustrated in FIGS. 6A and 6B, as body temperatures 608A and 608B of human subjects 601A and 601B are estimated based on the first and second distance-corrected thermal intensity values 606A and 606B.

An indication of a body temperature of a human subject may be estimated in any suitable way. As discussed above, thermal intensity values of pixels of a thermal image correspond to the relative temperatures of objects in an environment. Thus, in some cases, the computing device need not estimate an absolute, numerical body temperature of any particular human subject. Rather, in some cases, reporting an indication of a body temperature of a human subject may include outputting a notification that a particular human subject appears to have a meaningfully higher temperature than other human subjects, visible in a same or different thermal images.

Alternatively, in various examples, the computing device may use any suitable method for estimating the absolute, numerical body temperature of a human subject from distance-corrected thermal intensity values of a thermal image. Because the performance of a thermal camera is affected by a number of factors, including temperature, it can be difficult or impossible to correlate any particular thermal intensity value with a temperature value without an independent reference. Accordingly, in one example, the real-world environment may include a blackbody radiator having a predetermined temperature and thermal emissivity value.

Figure 7:
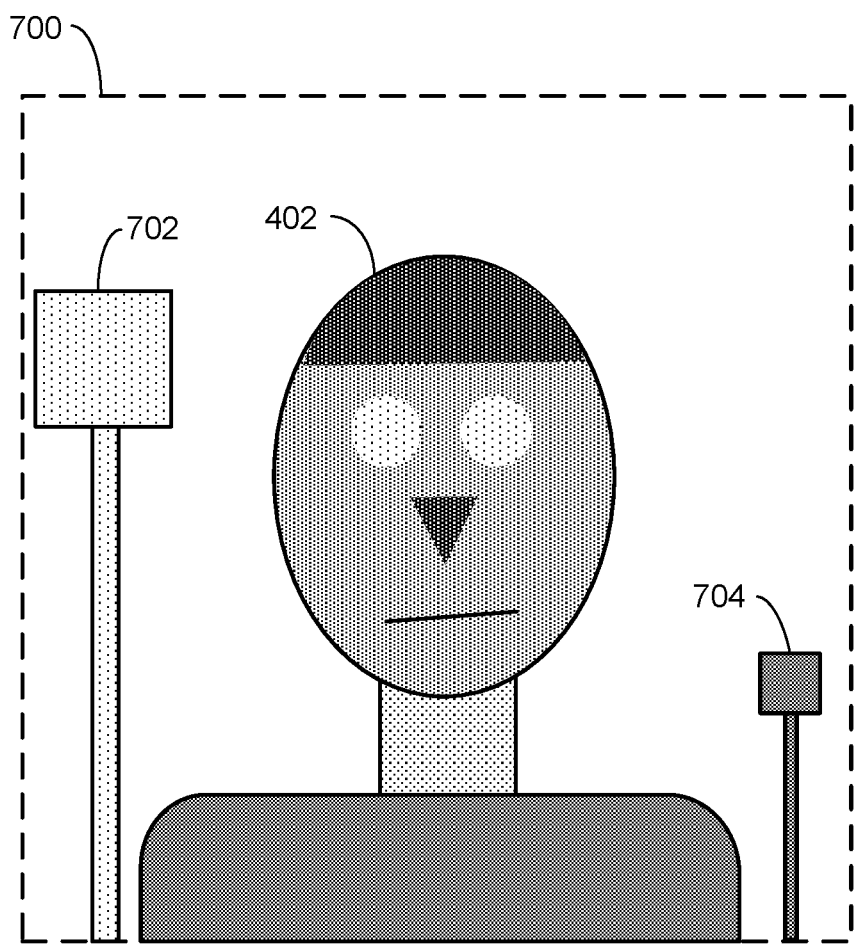
FIG. 7 schematically depicts an example thermal image depicting a human subject and two blackbody radiators.

This is schematically illustrated in FIG. 7, which shows another example thermal image 700, again depicting human subject 402. In this example, however, the thermal image also depicts a blackbody radiator 702. The blackbody radiator may have a predetermined temperature (e.g., 100° F.) and a known thermal emissivity value (e.g., 0.95). Thus, by evaluating thermal intensity values corresponding to the blackbody radiator, the computing device may determine a reference by which any particular thermal intensity values may be resolved to an absolute temperature. This may be done further based on a known sensitivity of the thermal camera—e.g., a known difference in grey-level count that corresponds to a known difference in temperature. In this manner, the temperature of any particular portion of the human subject may be estimated based on a comparison of the distance-corrected thermal intensity values for the human subject and thermal intensity values for the blackbody radiator, in tandem with the known temperature of the blackbody radiator. In other words, reporting the indication of the body temperature of a human subject may include comparing thermal intensity values of pixels corresponding to the blackbody radiator to distance-corrected thermal intensity values, as described above.

In some examples, the real-world environment may have two or more blackbody radiators each at different distances away from the thermal camera. The two or more blackbody radiators may have the same or different known temperatures, and the same or different known thermal emissivity values. This is also shown in FIG. 7, in which the real-world environment further includes a second blackbody radiator 704, at a greater distance away from the thermal camera than the first blackbody radiator 702. As such, when estimating a human subject's body temperature, the computing device may use as a reference whichever blackbody radiator is closest to the human subject.

A "blackbody radiator" as described herein may take any suitable form. The blackbody radiators depicted in FIG. 7 are shown schematically and are not limiting. Blackbody radiators may be composed of any suitable materials, have any shapes and sizes, and may have any suitable predetermined temperatures and thermal emissivity values.

In other examples, a real-world environment need not include a blackbody radiator for use as a reference. Rather, the computing device may derive a reference based on a plurality of other human subjects. For example, the computing device may identify the positions of a plurality of human faces in a plurality of thermal images. As discussed above, each of the plurality of human faces may correspond to pixels of respective thermal images having different thermal intensity values. The computing device may determine an average thermal intensity for the plurality of subjects, and compare distance-corrected thermal intensity values measured for future human subjects to this determined average. Any human subjects with distance-corrected thermal intensity values that significantly exceed the average (e.g., by two or more standard deviations) may be flagged. In other words, reporting an indication of the body temperature of a human subject may be further done based on a comparison of distance-corrected thermal intensity values for the human subject to an average thermal intensity of a plurality of other human faces. Again, this may be done in tandem with a known sensitivity of the thermal camera—e.g., a known difference in grey-count levels that corresponds to a known difference in temperature.

Figure 8:
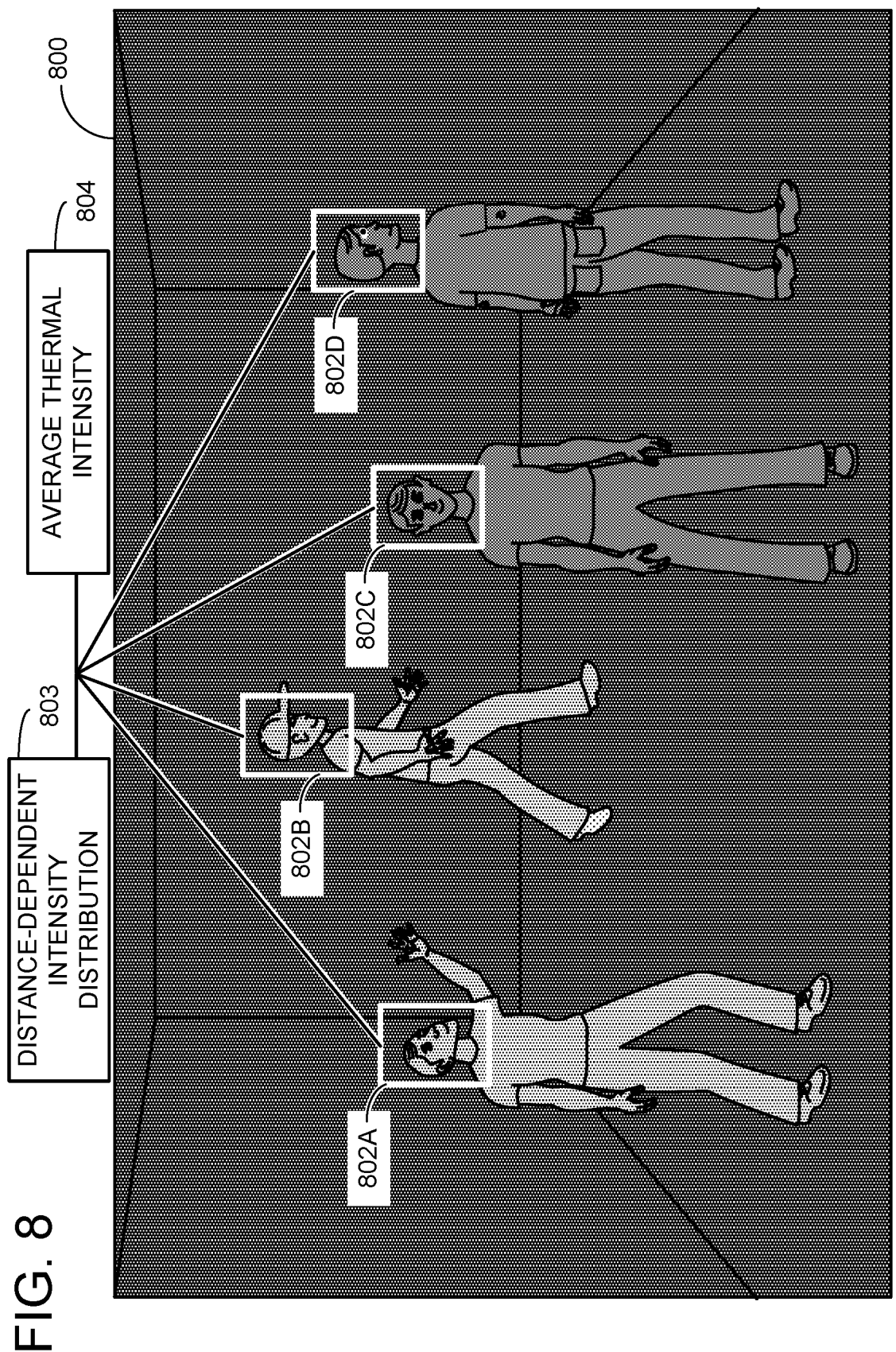
FIG. 8 schematically illustrates a thermal image including a plurality of human subjects.

This is schematically illustrated in FIG. 8, which shows another example thermal image 800. This thermal image includes a plurality of different human subjects 802A-802D. In this example, each of the human subjects are illustrated as if they have a uniform thermal intensity. It will be understood that this is done only for the sake of visual clarity, and that in practical scenarios, each human subject will have variable thermal intensity values across their body, as is the case for other thermal images described above.

In FIG. 8, the positions of the faces of the human subjects are identified, and thermal intensity values corresponding to the human faces are used to determine an average thermal intensity 804. As described above, in some cases the thermal intensity values used may correspond to the highest-intensity pixels for each subject (e.g., around the eye region), or any other suitable portion of each human subject may be used. The positions of the faces of each human subject may be identified in any suitable way—e.g., via comparison to a second image as discussed above.

In the example of FIG. 8, each of the plurality of human subjects are visible in a same thermal image 800. It will be understood that this is not limiting. Rather, in other examples, each of a plurality of human subjects used to determine an average thermal intensity may be identified in different thermal images. Furthermore, using an average thermal intensity as a reference in this manner is based on the assumption that most (if not all) of the human subjects have a normal body temperature (e.g., approximately 98.6° F.). Accordingly, if any human subjects are identified as having significantly higher or lower thermal intensity than other human subjects of the plurality, they may in some cases be excluded from the average thermal intensity as outliers. Once the average thermal intensity is determined, it may be presumed that the average thermal intensity corresponds to an average body temperature. Thus, any future thermal intensity values for a particular user that are significantly higher than the average may be indicate a fever.

In FIG. 8, each of the plurality of human subjects are disposed at different differences away from the thermal camera. As discussed above, in some cases the distance correction factor may be derived based on identifying a plurality of different human subjects at different distances from the thermal camera in a plurality of different thermal images, and determining a distance-dependent intensity distribution of thermal intensity values corresponding to the plurality of different human subjects. Accordingly, in FIG. 8, the computing device determines a distance between the thermal camera and each of the human subjects 802A-802D, and estimates a distance-dependent intensity distribution 803. Again, it may be assumed that each of the plurality of human subjects has an approximately normal body temperature, and thus differences in intensity between the human subjects may be attributed to distance-dependent intensity attenuation. The distance correction factor may be derived on this basis.

Alternatively, in cases where the distance correction factor is already known prior to calculation of the average thermal intensity, thermal intensity values corresponding to each human subject may undergo distance correction, as discussed above. In some cases, for the purposes of determining an average thermal intensity, the computing device may only consider human subjects having a predetermined distance from the thermal camera (e.g., 2 meters). Similarly, the thermal intensity values of the plurality of human subjects may in some cases be tone-corrected prior to calculation of the average thermal intensity, in the case where multiple different skin tones are represented in the plurality of human subjects.

Figure 9A:
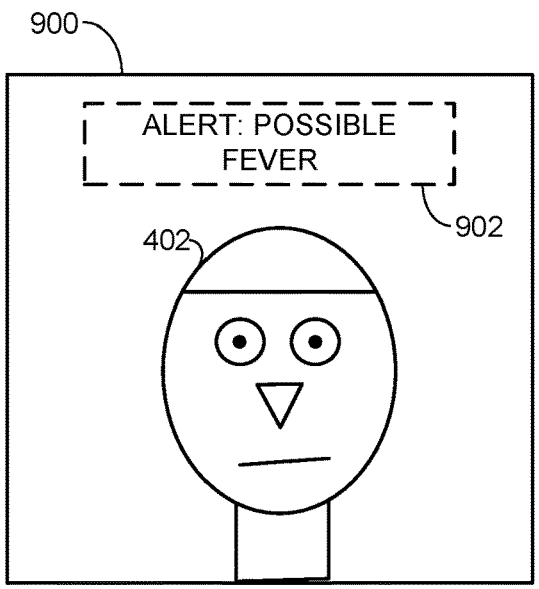
FIGS. 9A-9C schematically illustrate different example indications of a body temperature of a human subject.
Figure 9B:
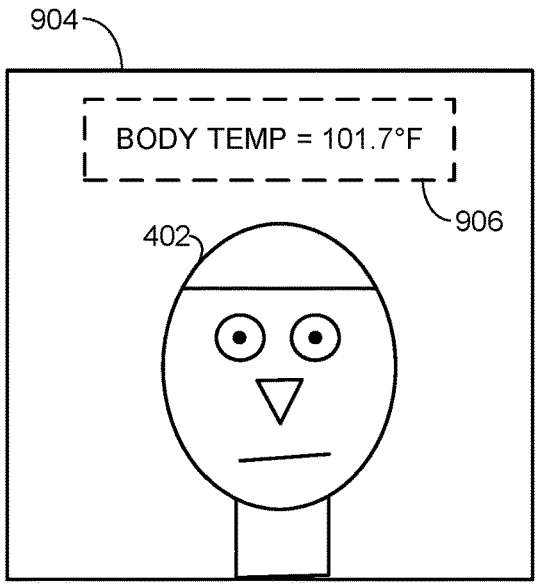
Figure 9C:
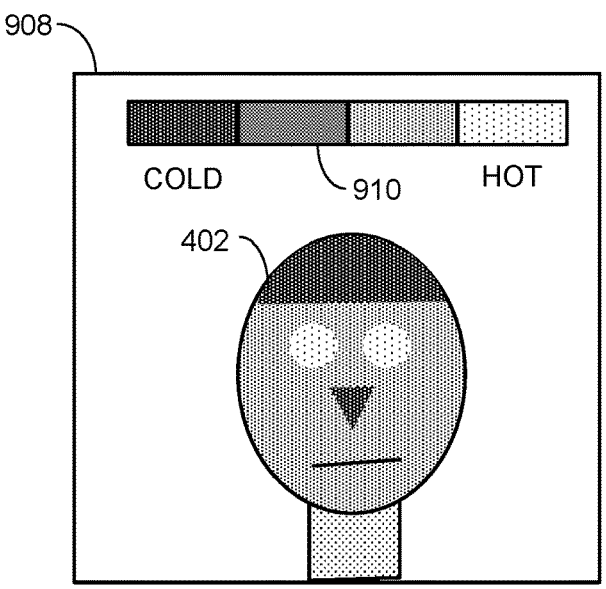

Once the body temperature of the human subject is estimated from distance-corrected thermal intensity values, an indication of the body temperature may be reported in any suitable way. FIGS. 9A-9C schematically depict various examples of ways in which an indication of a body temperature of a human subject may be reported. Specifically, FIG. 9A depicts an example displayed image 900, again showing human subject 402. Displayed image 900 may, for example, be a visible light image captured by a visible light camera. Displayed image 900 also includes a notification 902 that the body temperature of the human subject is estimated to exceed a predetermined fever threshold—e.g., 101° F. Any suitable fever threshold may be used. Furthermore, notification 902 is a non-limiting example. Other notifications may include any suitable information, and may take any suitable form, including non-visual forms—e.g., a different notification may be output as an audio alert.

FIG. 9B shows a different example displayed image 904, again taking the form of a visible light image depicting human subject 402. In this example, however, the indication of the body temperature of the human subject is reported via a notification 906, which incudes an absolute, numerical estimate of the human subject's body temperature. Again, notification 906 may take any suitable form and include any suitable information.

FIG. 9C shows a third example displayed image 908. In this example, the displayed image is a representation of a thermal image. In other words, pixels of displayed image 908 are based on thermal intensity values, rather than wavelengths of visible light. In some cases, the pixel values of a representation of a thermal image, such as displayed image 908, may differ from pixel values of an original thermal image—e.g., to make the displayed image easier for human users to parse. For instance, the scale of the thermal intensity values may be changed, or artificial colors may be used to represent the thermal intensity of the various pixels.

Displayed image 908 also includes a thermal reference 910, indicating to a human user the relative temperatures that each pixel of the thermal image correspond to. While different degrees of grey-scale shading are used in this example, this is not limiting. Rather, other examples may use spectra of visible light colors—e.g., a range from blue to red. In other words, the indication of the body temperature of the human subject may in some cases be reported via colors of pixels used to represent the human subject in the displayed image.

It will be understood that each of displayed images 900, 904, and 908 are non-limiting. In general, a displayed image may be a visible light image, a representation of a thermal image, or take any other suitable form. Furthermore, a displayed image may represent a human subject in any suitable way, and similarly report an estimated body temperature of the human subject in any suitable way. Displayed images may be presented using any suitable electronic display. For example, displayed images may be presented using a near-eye display (e.g., near-eye displays 110 or 302), or any other type of electronic display, including televisions, computer monitors, mobile device displays, etc.

The methods and processes described herein may be tied to a computing system of one or more computing devices. In particular, such methods and processes may be implemented as an executable computer-application program, a network-accessible computing service, an application-programming interface (API), a library, or a combination of the above and/or other compute resources.

Figure 10:
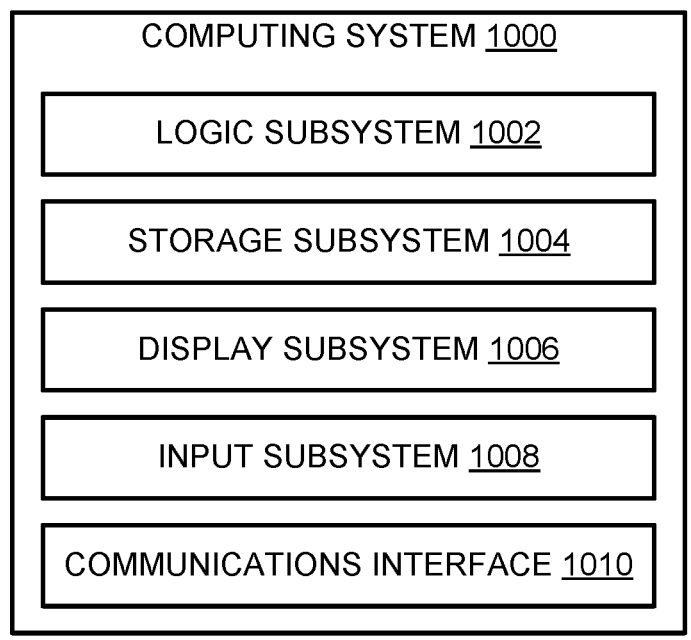
FIG. 10 schematically illustrates an example computing system.

FIG. 10 schematically shows a simplified representation of a computing system 1000 configured to provide any to all of the compute functionality described herein. Computing system 1000 may take the form of one or more personal computers, network-accessible server computers, tablet computers, home-entertainment computers, gaming devices, mobile computing devices, mobile communication devices (e.g., smart phone), virtual/augmented/mixed reality computing devices, wearable computing devices, Internet of Things (IoT) devices, embedded computing devices, and/or other computing devices.

Computing system 1000 includes a logic subsystem 1002 and a storage subsystem 1004. Computing system 1000 may optionally include a display subsystem 1006, input subsystem 1008, communication subsystem 1010, and/or other subsystems not shown in FIG. 10.

Logic subsystem 1002 includes one or more physical devices configured to execute instructions. For example, the logic subsystem may be configured to execute instructions that are part of one or more applications, services, or other logical constructs. The logic subsystem may include one or more hardware processors configured to execute software instructions. Additionally, or alternatively, the logic subsystem may include one or more hardware or firmware devices configured to execute hardware or firmware instructions. Processors of the logic subsystem may be single-core or multi-core, and the instructions executed thereon may be configured for sequential, parallel, and/or distributed processing. Individual components of the logic subsystem optionally may be distributed among two or more separate devices, which may be remotely located and/or configured for coordinated processing. Aspects of the logic subsystem may be virtualized and executed by remotely-accessible, networked computing devices configured in a cloud-computing configuration.

Storage subsystem 1004 includes one or more physical devices configured to temporarily and/or permanently hold computer information such as data and instructions executable by the logic subsystem. When the storage subsystem includes two or more devices, the devices may be collocated and/or remotely located. Storage subsystem 1004 may include volatile, nonvolatile, dynamic, static, read/write, read-only, random-access, sequential-access, location-addressable, file-addressable, and/or content-addressable devices. Storage subsystem 1004 may include removable and/or built-in devices. When the logic subsystem executes instructions, the state of storage subsystem 1004 may be transformed—e.g., to hold different data.

Aspects of logic subsystem 1002 and storage subsystem 1004 may be integrated together into one or more hardware-logic components. Such hardware-logic components may include program- and application-specific integrated circuits (PASIC/ASICs), program- and application-specific standard products (PSSP/ASSPs), system-on-a-chip (SOC), and complex programmable logic devices (CPLDs), for example.

The logic subsystem and the storage subsystem may cooperate to instantiate one or more logic machines. As used herein, the term "machine" is used to collectively refer to the combination of hardware, firmware, software, instructions, and/or any other components cooperating to provide computer functionality. In other words, "machines" are never abstract ideas and always have a tangible form. A machine may be instantiated by a single computing device, or a machine may include two or more sub-components instantiated by two or more different computing devices. In some implementations a machine includes a local component (e.g., software application executed by a computer processor) cooperating with a remote component (e.g., cloud computing service provided by a network of server computers). The software and/or other instructions that give a particular machine its functionality may optionally be saved as one or more unexecuted modules on one or more suitable storage devices.

When included, display subsystem 1006 may be used to present a visual representation of data held by storage subsystem 1004. This visual representation may take the form of a graphical user interface (GUI). Display subsystem 1006 may include one or more display devices utilizing virtually any type of technology. In some implementations, display subsystem may include one or more virtual-, augmented-, or mixed reality displays.

When included, input subsystem 1008 may comprise or interface with one or more input devices. An input device may include a sensor device or a user input device. Examples of user input devices include a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition.

When included, communication subsystem 1010 may be configured to communicatively couple computing system 1000 with one or more other computing devices. Communication subsystem 1010 may include wired and/or wireless communication devices compatible with one or more different communication protocols. The communication subsystem may be configured for communication via personal-, local- and/or wide-area networks.

This disclosure is presented by way of example and with reference to the associated drawing figures. Components, process steps, and other elements that may be substantially the same in one or more of the figures are identified coordinately and are described with minimal repetition. It will be noted, however, that elements identified coordinately may also differ to some degree. It will be further noted that some figures may be schematic and not drawn to scale. The various drawing scales, aspect ratios, and numbers of components shown in the figures may be purposely distorted to make certain features or relationships easier to see.

In an example, a method for estimating human body temperature comprises: receiving, via a thermal camera, a thermal image captured of a real-world environment, the thermal image including thermal intensity values for each of a plurality of pixels of the thermal image; identifying a position of a human face of a human subject within the thermal image; receiving an indication of a distance between the human subject and the thermal camera; applying, based on the distance between the human subject and the thermal camera, a distance correction factor to one or more thermal intensity values of one or more pixels corresponding to the human face to give one or more distance-corrected thermal intensity values; and based on the one or more distance-corrected thermal intensity values, reporting an indication of a body temperature of the human subject. In this example or any other example, the method further comprises: identifying a position of a second human face corresponding to a second human subject within the thermal image; receiving an indication of a second distance between the second human subject and the thermal camera; applying, based on the second distance between the second human subject and the thermal camera, a second distance correction factor to one or more thermal intensity values of one or more pixels corresponding to the second human face to give one or more second distance-corrected thermal intensity values; and based on the one or more second distance-corrected thermal intensity values, reporting an indication of a body temperature of the second human subject. In this example or any other example, the indication of the distance between the human subject and the thermal camera is received from a depth camera. In this example or any other example, the indication of the distance between the human subject and the thermal camera is received from a stereoscopic pair of visible light cameras. In this example or any other example, the distance correction factor is determined during factory calibration of the thermal camera. In this example or any other example, the distance correction factor is derived based on identifying a plurality of different human subjects at different distances from the thermal camera in a plurality of different thermal images, and determining a distance-dependent intensity distribution of thermal intensity values corresponding to the plurality of different human subjects. In this example or any other example, the distance correction factor is derived based on determining a distance-dependent intensity change of thermal intensity values corresponding to a reference human subject, as a distance between the reference human subject and the thermal camera changes over a plurality of thermal images. In this example or any other example, the method further comprises identifying a skin tone of the human subject, applying a skin tone correction factor to the one or more thermal intensity values to give tone-corrected thermal intensity values, and further reporting the indication of the body temperature of the human subject based on the tone-corrected thermal intensity values. In this example or any other example, the method further comprises receiving, via a second camera sensitive to a different spectrum of light from the thermal camera, a second image captured of the real-world environment, identifying a position of the first human face within the second image, and identifying the position of the first human face within the thermal image based on correspondences between the pixels of the second image and the pixels of the thermal image. In this example or any other example, the one or more pixels corresponding to the human face, having the thermal intensity values to which the distance correction factor is applied, include one or more highest-intensity pixels of the human face. In this example or any other example, reporting the indication of the body temperature of the human subject includes estimating an absolute body temperature of the human subject. In this example or any other example, the thermal intensity values are grey-level counts, and the absolute body temperature of the human subject is estimated based on a known sensitivity of the thermal camera. In this example or any other example, the absolute body temperature of the human subject is numerically represented on a near-eye display of a head-mounted display device, such that the absolute body temperature is displayed at a screen space position on the near-eye display at or near a position corresponding to the human subject. In this example or any other example, the method further comprises displaying a representation of the thermal image on an electronic display, and reporting the indication of the body temperature of the human subject via colors of pixels used to represent the human subject. In this example or any other example, reporting the indication of the body temperature of the human subject includes outputting a notification that the body temperature of the human subject is estimated to exceed a predetermined fever threshold. In this example or any other example, the real-world environment includes a blackbody radiator having a predetermined temperature and thermal emissivity value, and the indication of the body temperature of the human subject is further reported based on a comparison of thermal intensity values of one or more pixels corresponding to the blackbody radiator to the one or more distance-corrected thermal intensity values. In this example or any other example, the real-world environment includes two or more blackbody radiators at different distances away from the thermal camera, each of the two or more blackbody radiators having the predetermined temperature. In this example or any other example, the method further comprises: identifying positions of a plurality of human faces in a plurality of thermal images, each of the plurality of human faces corresponding to one or more pixels of respective thermal images having corresponding thermal intensity values; determining an average thermal intensity of the plurality of human faces; and reporting the indication of the body temperature of the human subject further based on a comparison of the average thermal intensity of the plurality of human faces to the one or more distance-corrected thermal intensity values.

In an example, a computing device comprises: a thermal camera; a logic machine; and a storage machine holding instructions executable by the logic machine to: receive, via the thermal camera, a thermal image captured of a real-world environment, the thermal image including thermal intensity values for each of a plurality of pixels of the thermal image; identify a position of a human face of a human subject within the thermal image; receive an indication of a distance between the human subject and the thermal camera; apply, based on the distance between the human subject and the thermal camera, a distance correction factor to one or more thermal intensity values of one or more pixels corresponding to the human face to give one or more distance-corrected thermal intensity values; and based on the one or more distance-corrected thermal intensity values, report an indication of a body temperature of the human subject.

In an example, a head-mounted display device comprises: a near-eye display; a thermal camera; a logic machine; and a storage machine holding instructions executable by the logic machine to: receive, via the thermal camera, a thermal image captured of a real-world environment, the thermal image including thermal intensity values for each of a plurality of pixels of the thermal image; identify a position of a human face within the thermal image, the human face corresponding to a human subject; receive an indication of a distance between the human subject and the thermal camera; apply, based on the distance between the human subject and the thermal camera, a distance correction factor to one or more thermal intensity values of one or more pixels corresponding to the human face to give one or more distance-corrected thermal intensity values; based on the one or more distance-corrected thermal intensity values, estimate an absolute body temperature of the human subject; and numerically display the absolute body temperature of the human subject at a screen space position on the near-eye display at or near a position corresponding to the human subject.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The invention claimed is:

1. A method for estimating human body temperature, the method comprising:
  receiving, via a thermal camera, a thermal image captured of a real-world environment, the thermal image including thermal intensity values for each of a plurality of pixels of the thermal image;
  identifying a position of a human face of a human subject within the thermal image;
  receiving an indication of a distance between the human subject and the thermal camera;
  applying, based on the distance between the human subject and the thermal camera, a distance correction factor to one or more thermal intensity values of one or more pixels corresponding to the human face to give one or more distance-corrected thermal intensity values, such that the one or more thermal intensity values of the one or more pixels corresponding to the human face in the thermal image are changed as a function of the distance between the human subject and the thermal camera to give the one or more distance-corrected thermal intensity values; and
  based on the one or more distance-corrected thermal intensity values, reporting an indication of a body temperature of the human subject.

2. The method of claim 1, further comprising:
  identifying a position of a second human face corresponding to a second human subject within the thermal image;
  receiving an indication of a second distance between the second human subject and the thermal camera;
  applying, based on the second distance between the second human subject and the thermal camera, a second distance correction factor to one or more thermal intensity values of one or more pixels corresponding to the second human face in the thermal image to give one or more second distance-corrected thermal intensity values, such that the one or more thermal intensity values of the one or more pixels corresponding to the second human face are changed as a function of the second distance between the second human subject and the thermal camera to give the one or more second distance-corrected thermal intensity values; and based on the one or more second distance-corrected thermal intensity values, reporting an indication of a body temperature of the second human subject.

3. The method of claim 1, where the indication of the distance between the human subject and the thermal camera is received from a depth camera.

4. The method of claim 1, where the indication of the distance between the human subject and the thermal camera is received from a stereoscopic pair of visible light cameras.

5. The method of claim 1, where the distance correction factor is determined during factory calibration of the thermal camera.

6. The method of claim 1, where the distance correction factor is derived based on identifying a plurality of different human subjects at different distances from the thermal camera in a plurality of different thermal images, and determining a distance-dependent intensity distribution of thermal intensity values corresponding to the plurality of different human subjects.

7. The method of claim 1, where the distance correction factor is derived based on determining a distance-dependent intensity change of thermal intensity values corresponding to a reference human subject, as a distance between the reference human subject and the thermal camera changes over a plurality of thermal images.

8. The method of claim 1, further comprising identifying a skin tone of the human subject, applying a skin tone correction factor to the one or more thermal intensity values to give tone-corrected thermal intensity values, and further reporting the indication of the body temperature of the human subject based on the tone-corrected thermal intensity values.

9. The method of claim 1, further comprising receiving, via a second camera sensitive to a different spectrum of light from the thermal camera, a second image captured of the real-world environment, identifying a position of the first human face within the second image, and identifying the position of the first human face within the thermal image based on correspondences between the pixels of the second image and the pixels of the thermal image.

10. The method of claim 1, where the one or more pixels corresponding to the human face, having the thermal intensity values to which the distance correction factor is applied, include one or more highest-intensity pixels of the human face.

11. The method of claim 1, where reporting the indication of the body temperature of the human subject includes estimating an absolute body temperature of the human subject.

12. The method of claim 11, where the thermal intensity values are grey-level counts, and the absolute body temperature of the human subject is estimated based on a known sensitivity of the thermal camera.

13. The method of claim 11, where the absolute body temperature of the human subject is numerically represented on a near-eye display of a head-mounted display device, such that the absolute body temperature is displayed at a screen space position on the near-eye display at or near a position corresponding to the human subject.

14. The method of claim 1, further comprising displaying a representation of the thermal image on an electronic display, and reporting the indication of the body temperature of the human subject via colors of pixels used to represent the human subject.

15. The method of claim 1, where reporting the indication of the body temperature of the human subject includes outputting a notification that the body temperature of the human subject is estimated to exceed a predetermined fever threshold.

16. The method of claim 1, where the real-world environment includes a blackbody radiator having a predetermined temperature and thermal emissivity value, and the indication of the body temperature of the human subject is further reported based on a comparison of thermal intensity values of one or more pixels corresponding to the blackbody radiator to the one or more distance-corrected thermal intensity values.

17. The method of claim 16, where the real-world environment includes two or more blackbody radiators at different distances away from the thermal camera, each of the two or more blackbody radiators having the predetermined temperature.

18. The method of claim 1, further comprising:
identifying positions of a plurality of human faces in a plurality of thermal images, each of the plurality of human faces corresponding to one or more pixels of respective thermal images having corresponding thermal intensity values;
determining an average thermal intensity of the plurality of human faces; and
reporting the indication of the body temperature of the human subject further based on a comparison of the average thermal intensity of the plurality of human faces to the one or more distance-corrected thermal intensity values.

19. A computing device, comprising:
a thermal camera;
a logic machine; and
a storage machine holding instructions executable by the logic machine to:
receive, via the thermal camera, a thermal image captured of a real-world environment, the thermal image including thermal intensity values for each of a plurality of pixels of the thermal image;
identify a position of a human face of a human subject within the thermal image;
receive an indication of a distance between the human subject and the thermal camera;
apply, based on the distance between the human subject and the thermal camera, a distance correction factor to one or more thermal intensity values of one or more pixels corresponding to the human face to give one or more distance-corrected thermal intensity values, such that the one or more thermal intensity values of the one or more pixels corresponding to the human face in the thermal image are changed as a function of the distance between the human subject and the thermal camera to give the one or more distance-corrected thermal intensity values; and
based on the one or more distance-corrected thermal intensity values, report an indication of a body temperature of the human subject.

20. A head-mounted display device, comprising:
a near-eye display;
a thermal camera;
a logic machine; and
a storage machine holding instructions executable by the logic machine to:
receive, via the thermal camera, a thermal image captured of a real-world environment, the thermal image including thermal intensity values for each of a plurality of pixels of the thermal image;

identify a position of a human face within the thermal image, the human face corresponding to a human subject;

receive an indication of a distance between the human subject and the thermal camera;

apply, based on the distance between the human subject and the thermal camera, a distance correction factor to one or more thermal intensity values of one or more pixels corresponding to the human face to give one or more distance-corrected thermal intensity values, such that the one or more thermal intensity values of the one or more pixels corresponding to the human face in the thermal image are changed as a function of the distance between the human subject and the thermal camera to give the one or more distance-corrected thermal intensity values;

based on the one or more distance-corrected thermal intensity values, estimate an absolute body temperature of the human subject; and numerically display the absolute body temperature of the human subject at a screen space position on the near-eye display at or near a position corresponding to the human subject.

\* \* \* \* \*